United States Patent [19]

Organ et al.

[11] Patent Number: 5,284,877
[45] Date of Patent: Feb. 8, 1994

[54] ALKYL AND ALKENYL MACROLIDES HAVING IMMUNOSUPPRESSIVE ACTIVITY

[75] Inventors: Helen M. Organ, Roselle Park; Mark A. Holmes, Edison; Judith M. Pisano, Cliffside Park; Matthew J. Wyvratt, Mountainside, all of N.J.

[73] Assignee: Merck & Co., Inc., Rahway, N.J.

[21] Appl. No.: 897,711

[22] Filed: Jun. 12, 1992

[51] Int. Cl.$^5$ .................. A61K 31/395; C07D 267/00
[52] U.S. Cl. .................................. 518/183; 514/291; 514/411; 540/455; 540/456
[58] Field of Search ................ 540/455, 456; 514/183, 514/291, 411

[56] References Cited

U.S. PATENT DOCUMENTS

| | | | |
|---|---|---|---|
| 4,894,366 | 1/1990 | Okuhara et al. | 514/63 |
| 4,929,611 | 5/1990 | Okuhara et al. | 514/183 |
| 4,956,352 | 9/1990 | Okuhara et al. | 514/63 |
| 4,981,792 | 1/1991 | Inamine et al. | 435/119 |
| 5,011,844 | 4/1991 | Fehr | 514/291 |
| 5,064,835 | 11/1991 | Bochis et al. | 514/291 |
| 5,110,811 | 5/1992 | Okuhara et al. | 514/183 |

FOREIGN PATENT DOCUMENTS

| | | |
|---|---|---|
| 0349061 | 1/1990 | European Pat. Off. |
| 0353678 | 2/1990 | European Pat. Off. |
| 0388152 | 9/1990 | European Pat. Off. |
| 0402931 | 12/1990 | European Pat. Off. |
| 0413532 | 2/1991 | European Pat. Off. |
| 0427680 | 5/1991 | European Pat. Off. |

(List continued on next page.)

OTHER PUBLICATIONS

Tanaka, et al., J. Am. Chem. Soc., 1987, 109 5031–5033.

Primary Examiner—John M. Ford
Assistant Examiner—Y. N. Gupta
Attorney, Agent, or Firm—Charles M. Caruso; J. Eric Thies

[57] ABSTRACT

Alkyl and alkenyl macrolides of the general structural Formula I:

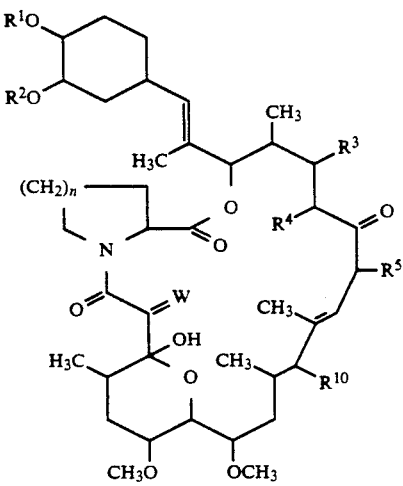

have been prepared from suitable precursors by oxidation and derivitization at C-17. These macrolide immunosuppressants are useful in a mammalian host for the treatment of autoimmune diseases, infectious diseases and/or the prevention of rejection of foreign organ transplants. In addition, these macrolide immunosuppressants are useful in the topical treatment of inflammatory and hyperproliferative skin diseases and cutaneous manifestations of immunologically-mediated illnesses. Also, these macrolides are useful in the treatment of reversible obstructive airways disease, particularly asthma; as hair revitalizing agents, especially in the treatment of male pattern alopecia oralopecia senilis; in the reversal of multidrug resistance of tumor cells; in treatment of inflammation of mucosa and blood vessels, gastric ulcers, vascular damage, ischemic bowel disease, inflammatory bowel disease, necrotizing enterocolitis, intestinal lesions associated with thermal burns; in the treatment of cytomegalovirus infection; and in the treatment of idiopathic thrombocytopenic purpura and Basedow's disease.

8 Claims, No Drawings

FOREIGN PATENT DOCUMENTS

| | | |
|---|---|---|
| 0428365 | 5/1991 | European Pat. Off. . |
| 0463690 | 1/1992 | European Pat. Off. . |
| 2245891A | 1/1992 | United Kingdom . |
| WO89/05304 | 6/1989 | World Int. Prop. O. . |
| WO91/02736 | 3/1991 | World Int. Prop. O. . |
| WO91/04025 | 4/1991 | World Int. Prop. O. . |
| WO91/13889 | 9/1991 | World Int. Prop. O. . |
| WO91/13899 | 9/1991 | World Int. Prop. O. . |
| WO92/00313 | 1/1992 | World Int. Prop. O. . |
| WO92/00980 | 1/1992 | World Int. Prop. O. . |
| WO92/03441 | 3/1992 | World Int. Prop. O. . |
| WO92/05179 | 4/1992 | World Int. Prop. O. . |

ALKYL AND ALKENYL MACROLIDES HAVING IMMUNOSUPPRESSIVE ACTIVITY

SUMMARY OF THE INVENTION

The present invention is related to alkyl and alkenyl macrolides which are useful in a mammalian host for the treatment of autoimmune diseases (such as juvenile-onset diabetes mellitus, multiple sclerosis and rheumatoid arthritis), immunodepression, infectious diseases and/or the prevention of rejection of foreign organ transplants, e.g. bone marrow and heart transplants and are also useful in the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vascultides, erythemas, cutaneous eosinophilias, Lupus erythematosus, Alopecia areata), male pattern alopecia, alopecia senilis, reversible obstructive airways disease, particularly asthma, alopecia, inflammation of mucosa and blood vessels, cytomegalovirus infection, multidrug resistance, idiopathic thrombocytopenic purpura, and/or hepatic injury associated with ischemia. In addition, some of the compounds of this invention may have antagonistic properties and so have utility in the reversal of immunosuppressive activity and/or diminishing the toxicity of other immunosuppressive agents.

More particularly, this invention relates to compounds of the general structural formula I:

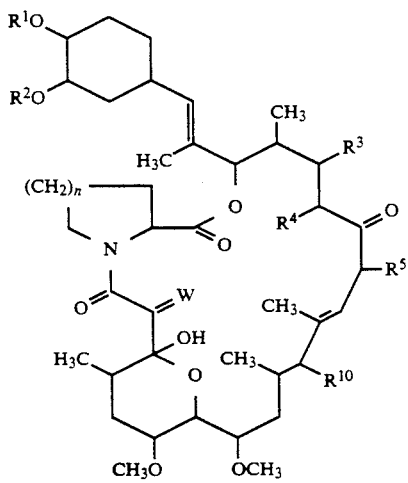

wherein $R^1$, $R^2$, $R^3$, $R^4$, $R^5$, $R^{10}$, W and n are hereinafter defined.

This invention also relates to pharmaceutical compositions containing the compounds and to a method of use of the present compounds and other agents for the treatment of and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (*J. Am. Chem. Soc.*, 1987, 109, 5031 and *J. Antibiotics* 1987, 40, 1249) disclose 17-allyl-1,14-dihydroxy-12-[2'-(4"-hydroxy-3"-methoxycylohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506), (FK-506), (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compounds which are the starting materials for the preparation of the compounds described. The synthetic preparation of the aforementioned starting material (FR-900506) has recently been reported (*J. Am. Chem. Soc.*, 1989, 111, 1157). A Sandoz European patent application (EPO Publication No. 0,356,399) discloses stereoisomers of FR-900506 and derivatives at the 17-position. Fisons European and WIPO patent applications (EPO Publication No. 0,323,042 and PCT Publication No. WO 89/05304) discloses various derivatives of FR-900506, FR-900520 and related compounds. A Sandoz European Patent application (EPO Publication No. 0,437,680) discloses chloro, bromo, iodo and azido derivatives of FR-900506, FR-900520 and related compounds. A Merck European Patent application (EPO Publication No. 0,428,365) discloses various amino derivatives of FR-900506, FR-900520 and related compounds. A Fujisawa patent application (UK Publication No. GB 2,245,891-A) discloses various derivatives of FR-900506 bearing a heterocyclic group. Fujisawa patent applications (PCT Publication Nos. WO 92/00313 and WO 92/00980) disclose various derivatives of FR-900506 at the 17-position.

Fujisawa United States patents (U.S. Pat. No. 4,929,611, issued May 29, 1990 and U.S. Pat. No. 4,956,352, issued Sep. 11, 1990) discloses the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons WIPO patent application (PCT Publication No. WO 91/04025) discloses the use of various derivatives of FR-900506 in the treatment of immunodepression. A Fisons WIPO patent application (PCT Publication WO 90/14826) discloses the use of FR-900506 and related compounds in the treatment of reversible obstructive airways disease, particularly asthma. A Fujisawa European patent application (EPO Publication No. 0,423,714) discloses the use of FK-506 and derivatives as hair revitalizing agents. Various studies have suggested the efficacy of FK-506 in the treatment of a number of ailments, including rheumatoid arthritis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomeralonephritis (J. McCauley, et al., *Lancet*, 1990, 335, 674) and systemic lupus erythematosus (K. Takabayashi, et al., *Clin. Immunol. Immunopathol.*, 1989, 51, 110–117) multidrug resistance (M. Naito, et al., *Cancer Chemother. Pharmacol.*, 1992, 29, 195–200), inflammation of mucosa and blood vessels (PCT Publication WO 91/17754), cytomegalovirus infection (UK Publication GB 2,247,620A), and idiopathic thrombocytophenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and other disorders such as Chrons disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppresive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506, FK-506,

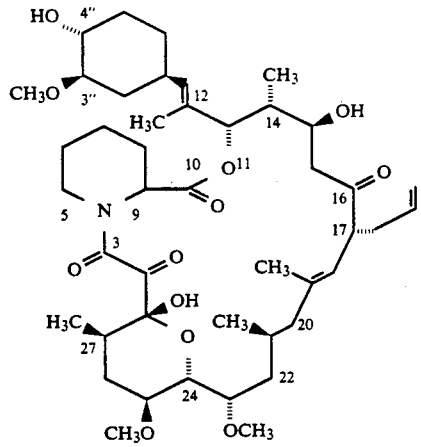

(17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]-octacos-18-ene-2,3,10,16-tetraone) and related compounds which were isolated and characterized by Tanaka, Kuroda, and co-workers at Fujisawa Pharmaceutical Co. in Japan, see *J. Am. Chem. Soc.*, 1987, 109, 5031, and U.S. Pat. No. 4,894,366, issued Jan. 16, 1990) have been shown to possess exceptional immunosuppressive activity. A Fujisawa United States patents (U.S. Pat. No. 4,929,611, issued May 29, 1990 U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthitis (C. Arita, et al., *Clincial exp. Immunol.*, 1990, 82, 456–461; N. Inamura, et al., *Clin. Immunol. Immunopathol.* 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K, Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117) multidrug resistance (M. Naito, et al., *Cancer Chemother. Pharmacol.*, 1992, 29, 195–200), inflammation of mucosa and blood vessels (PCT Publication WO 92/17754), cytomegalovirus infection (UK Publication GB 2,247,620A), and idiopathic thrombocytophenic purpura and Basedow's disease (PCT Publication WO 91/19495).

DETAILED DESCRIPTION OF THE INVENTION

A. Scope of the Invention

The novel compound of this invention has structural Formula I:

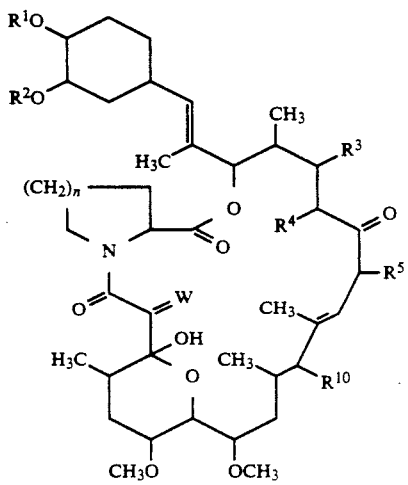

I or a pharmaceutically acceptable salt thereof, wherein:

$R^1$ is selected from:
(1) hydrogen; and
(2) $C_{1-4}$ alkanoyl;

$R^2$ is selected from:
(1) methyl; and
(2) hydrogen;

$R^3$ is hydrogen, hydroxy, or $C_{1-6}$alkoxy;

$R^4$ is hydrogen, or $R^3$ and $R^4$ taken together form a double bond;

$R^5$ is selected from:
(1) $C_{4-8}$ alkyl unsubstituted or substituted with one or more substituents selected from:
  (a) phenyl,
  (b) hydroxy,
  (c) halo,
  (d) —CHO,
  (e) —$CO_2H$,
  (f) —$CO_2$—$C_{1-6}$alkyl;
(2) $C_{4-8}$ alkenyl;
(3) $C_{3-8}$ alkenyl substituted with one or more substituents selected from:
  (a) phenyl,
  (b) hydroxy,
  (c) halo,
  (d) —CHO,
  (e) —$CO_2H$,
  (f) —$CO_2$—$C_{1-6}$alkyl;

$R^{10}$ is hydrogen, hydroxy, or fluoro;
W is O or (H, OH);
n is 1 or 2.

The compounds of the present invention have asymmetric centers and this invention includes all of the optical isomers and mixtures thereof.

In addition compounds with carbon—carbon double bonds may occur in Z- and E-forms with all isomeric forms of the compounds being included in the present invention.

When any variable (e.g., alkyl, aryl, $R^6$, $R^7$, $R^8$, $R^9$, $R^{10}$, $R^{11}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include configuration and at least one unsaturation, which may occur at any point along the chain, such as ethenyl, propenyl, butenyl, pentenyl, dimethylpentyl, and the like, and includes E and Z forms, where applicable. "Halo", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium.

Preferred compounds of the present invention include those of structural formula:

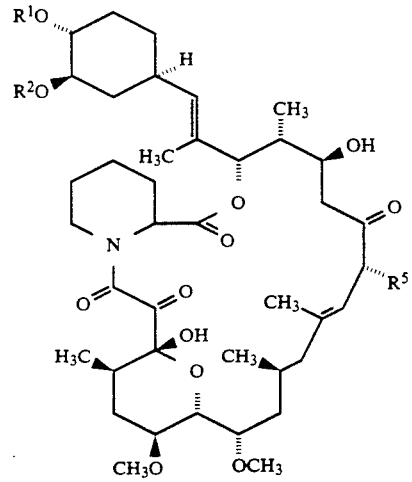

wherein $R^1$, $R^2$ and $R^5$ are selected from the following combinations of substituents:

|     | $R^1$ | $R^2$ | $R^5$ |
| --- | --- | --- | --- |
| (a) | H | $CH_3$ | ⤳$CO_2Et$ |
| (b) | H | $CH_3$ | ⤳$CO_2Et$ |
| (c) | H | $CH_3$ | ⤳$CO_2Me$ |

-continued

| | R¹ | R² | R⁵ |
|---|---|---|---|
| (d) | H | CH₃ | -CH₂-CH=CH-CHO |
| (e) | H | CH₃ | -CH₂-CH=CH-C(=O)-CH₃ |
| (f) | H | CH₃ | -CH₂-CH₂-C(=O)-CH₃ |
| (g) | H | CH₃ | -CH₂-CH=CH-CH₂-OH |
| (h) | H | CH₃ | -CH₂-CH=CCl₂ |
| (i) | H | CH₃ | -CH₂-CH=CBr₂ |
| (j) | H | CH₃ | -CH₂-CH=CH-C₆H₅ |
| (k) | H | CH₃ | -CH₂-CH=CH-CH=CH₂ |
| (l) | H | CH₃ | -CH₂-CH₂-CH=CH₂ |
| (m) | H | CH₃ | -CH₂-CH=CH-CH₂-CH₃ |
| (n) | H | CH₃ | -CH₂-CH=CH-CH₂-CH₂-CH₂-CH₃ |
| (o) | H | CH₃ | -CH₂-CH₂-CH=CH-CH₂-CH₃ |
| (p) | H | CH₃ | -CH₂-CH=C(CH₃)₂ |
| (q) | H | CH₃ | -CH₂-CH₂-CH₂-CH=CH₂ |
| (r) | H | CH₃ | -CH₂-CH₂-CH=CH-CH₃ |
| (s) | H | CH₃ | -CH₂-CH₂-CH₂-CH₂-CH₃ |

Preferred compounds of the present invention are the compounds identified as follows:

17-[(1'''-carboethoxy)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#1)

17-[(1'''-carbomethoxy)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#2)

17-[(2'''-carboethoxy)but-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#3)

17-[1'''-oxobut-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#4)

17-[2'''-oxopent-3'''-en-5'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#5)

17-[2'''-oxopent-5'''-yl]-1,14-dihydroxy-12-[2'(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#6)

17-[1'''-hydroxybut-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#7)

17-(1''',1'''-dibromo)allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#8)

17-(1''',1'''-dichloro)allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#9)

17-[(1'''-phenyl)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#10)

17-[pent-1''',3'''-dien-5'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#11)

17-[but-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#12)

17-[hex-4'''-en-6'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#13)

17-[oct-6'''-en-8'''-yl]--1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone; (#14)

17-[pent-3'''-en-5'''-yl]--1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#15)

17-[(1''',1'''-dimethyl)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone; (#16)

17-[1-butyl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo-[22.3.1.0$^{4,9}$]octacos-18-ene-2,3,10,16-tetraone; (#17)

17-[1-pentyl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo-[22.3.1.0$^{4,9}$]octacos-18-ene-2,3,10,16-tetraone; (#18)

17-[but-1'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclclo[22.3.1.0$^{4,9}$]octacos-18-ene-2,3,10,16-tetraone (#19).

B. Preparation of Compounds Within the Scope of the Present Invention

The starting materials for the preparation of the compounds of this invention are represented by Formula II:

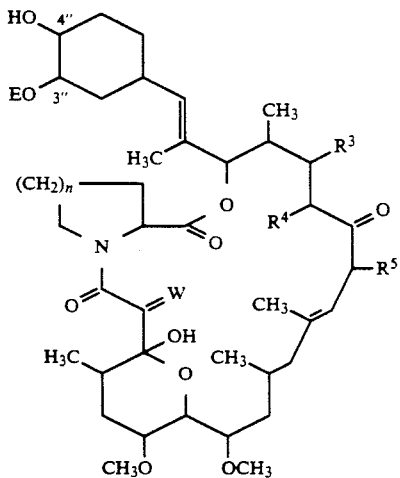

wherein:
E is hydrogen or methyl;
W is O or (H, OH);
R$^3$ is hydrogen, hydroxy, or C$_{1-6}$ alkoxy;
R$^4$ is hydrogen, or R$^3$ and R$^4$ taken together form a double bond;
R$^5$ is methyl, ethyl, propyl or allyl; and
n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042,; EPO Publication No. 0,356,399; PBJ Disclosure 63-17884; *J. Am. Chem. Soc.*, 1987, 109, 5031; *J. Antibiotics*, 1987, 40, 1249; *J. Antibiotics*, 1988, 41(1), 1592; and *J. Antibiotics*, 1992, 45(1), 118). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the art as the method to produce compounds of Formula II. Organisms belonging to the genus Streptomyces such as *Streptomyces tsukubaensis*, No. 9993 and *Streptomyces hygroscopicus*, var. *ascomycetis*, No. 14891 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where E is methyl, W is O, R$^3$ is hydroxyl, R$^4$ is hydrogen, R$^5$ is allyl and n is 2; (B) where E is methyl, W is O, R$^3$ is hydroxyl, R$^4$ is hydrogen, R$^5$ is ethyl and n is 2; (C) where E is methyl, W is O, R$^3$ is hydroxyl, R$^4$ is hydrogen, R$^5$ is methyl and n is 2; and (D) where E is methyl W is O, R$^3$ is hydroxyl, R$^4$ is hydrogen, R$^5$ is allyl and n is 1.

A lyophilized sample of the isolated *Streptomyces tsukubaensis*, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of R$^5$ may be conveniently reduced to propyl by well known methods, for example as described in U.S. Pat. No. 4,894,366. The hydroxy of R$^3$ may be protected by well known methods, for example as disclosed in EPO Publication No. 0,323,042. Likewise, the hydroxyl at C-4'' may also be protected. In addition, the hydroxy of R$^3$ may be reduced to a hydrogen or eliminated to form a double bond with R$^4$ (by methods disclosed in U.S. Pat. No. 4,894,366, EPO Publication No. 0,323,042 or EPO Publication No. 0,413,532). The carbonyl of W may be reduced to the alcohol by methods disclosed in EPO Publication No. 0,323,042 or by methods disclosed in EPO Publication No. 0,445,975. The hydroxy of R$^{10}$ may be introduced by methods disclosed in EPO Publication No. 0,463,690.

The methyl of E as produced may be replaced with hydrogen or demethylated and subsequently protected as desired, if necessary. This demethylation of compounds wherein E is methyl may be carried out in a fermentation reaction using the compounds of Formula II as a feedstock. For instance, compound A named under Formula II above may be demethylated at E above by using the microorganism Actinomycetales ATCC No. 53771 (described in U.S. Pat. No. 4,8981,792) or by using the microorganism *Streptomyces tsukubaensis*, No. 9993 (described in EPO Publication No. 0,353,678). Similarly, compound B named under Formula II above may be demethylated at E above using the microorganism Actinoplanacete sp. ATCC No. 53771 (described in EPO Publication No. 0,349,061). In addition the compound of Formula II wherein E is H, W is O, R$^3$ is hydroxy, R$^4$ is hydrogen, R$^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication No. 0,388,152). Similarly, the compound of Formula II wherein E is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (EPO Publication No. 0,388,153). The hydroxy of C-3″ may be protected by methods similar to those known for the protection of the hydroxyl groups of $R^3$ and/or C-4‴, for example as disclosed in U.S. Pat. No. 4,894,366.

Suitable protecting groups for hydroxyl include those groups well known in the art such as: methylthiomethyl, ethylthiomethyl; trisubstituted silyl such as trimethylsilyl, triethylsilyl, tributylsilyl, tri-i-propylsilyl, t-butyldimethylsilyl, tri-t-butylsilyl, methyldiphenylsilyl, ethyldiphenylsilyl, t-butyldiphenylsilyl, and the like; acyl such as acetyl, pivaloyl benzoyl, 4-methoxybenzoyl, 4-nitrobenzoyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, dated Jan. 16, 1990 and U.S. Pat. No. 4,929,611, issued May 29, 1990.

The novel processes for preparing the novel compounds of the present invention are illustrated as follows, wherein $R^1$, $R^2$, $R^3$, $R^5$, $R^6$, $R^7$, $R^8$, $R^9$, $R^{10}$, $R^{11}$, E, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

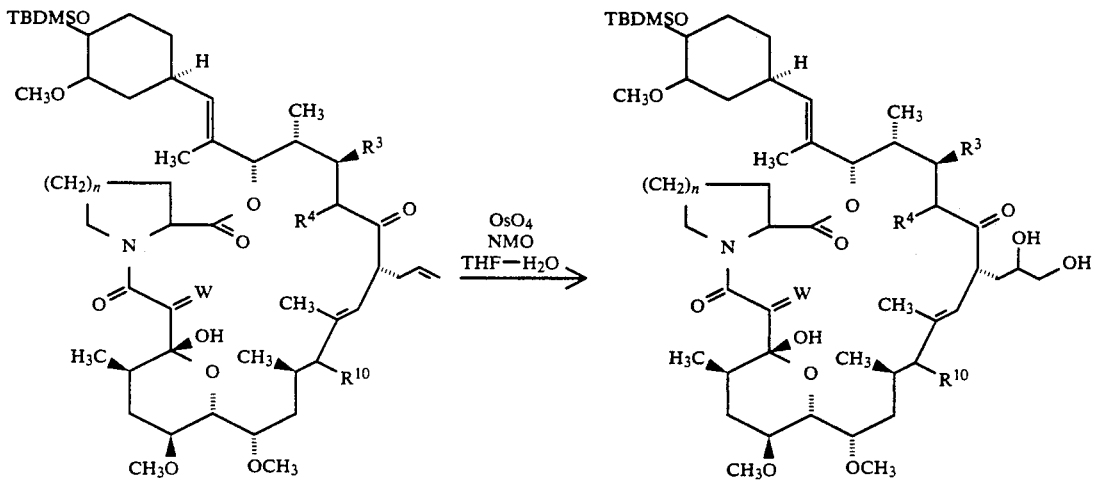

REACTION SCHEME B

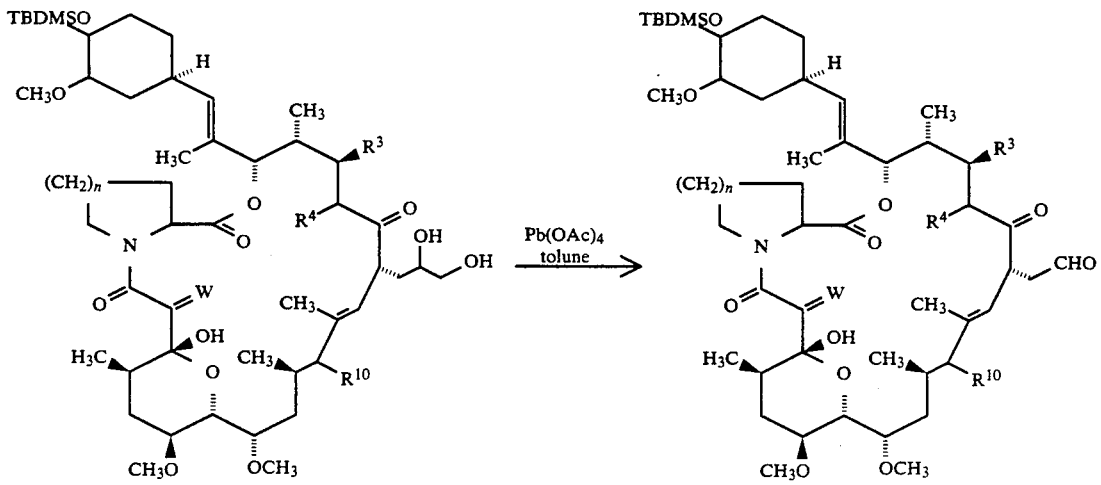

REACTION SCHEME C
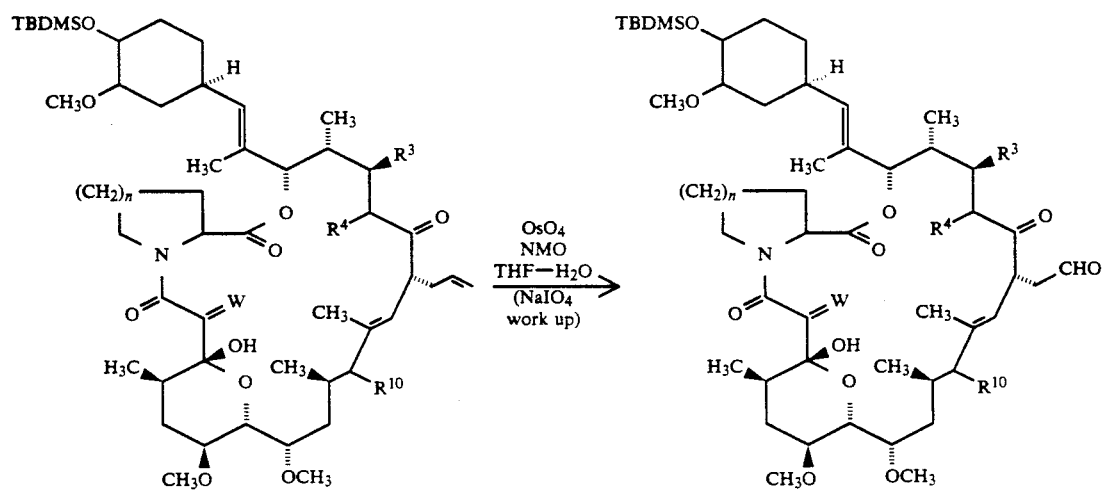
REACTION SCHEME D
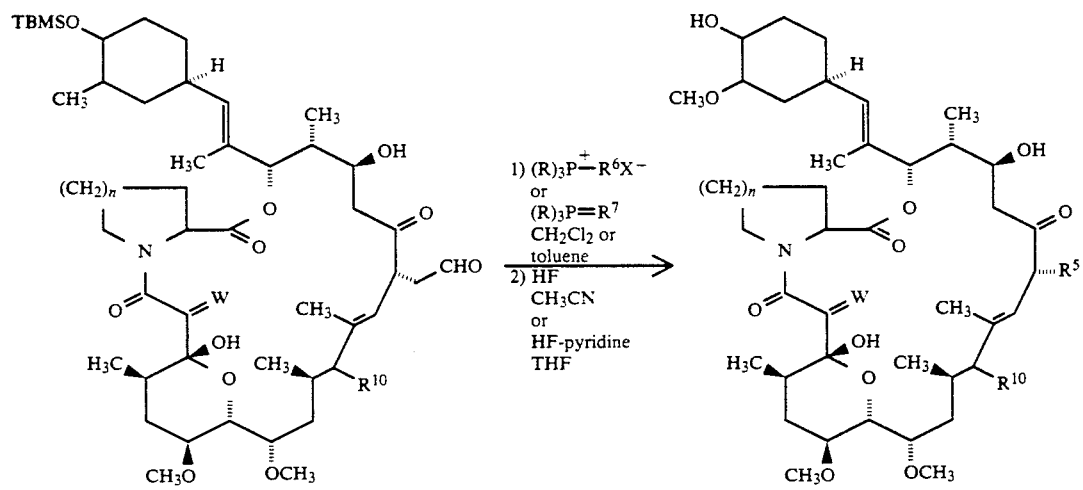
REACTION SCHEME E
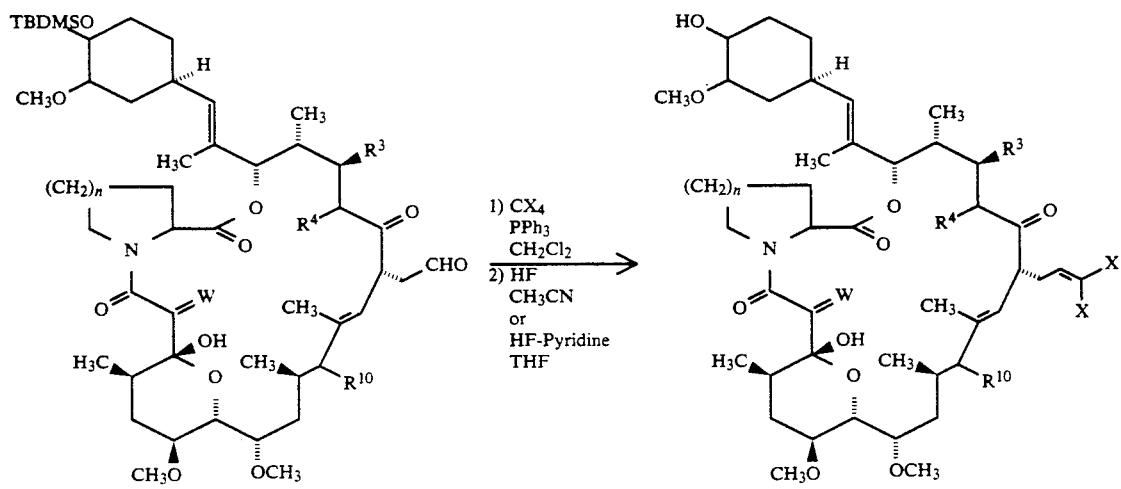

REACTION SCHEME F

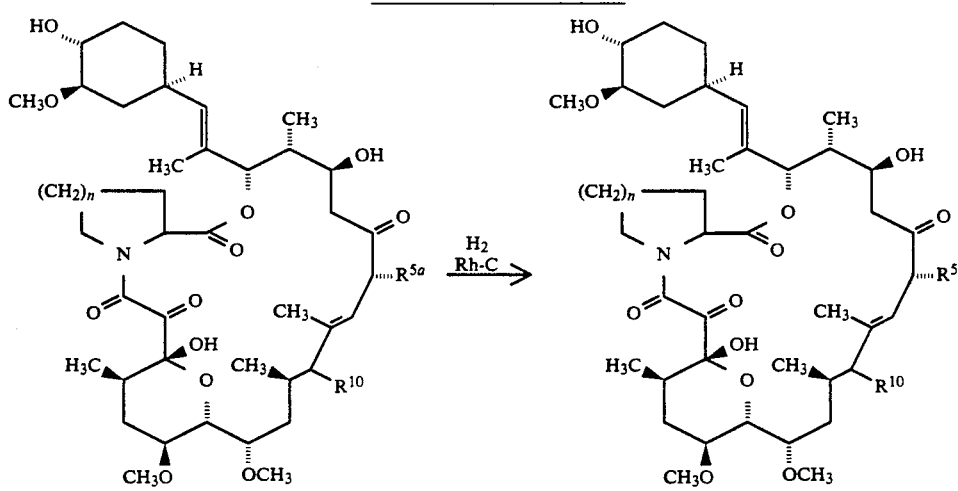

Reaction Scheme A:

As shown in Reaction Scheme A, a solution of the protected alkenyl-substituted macrolide is treated with osmium tetroxide, preferably in catalytic amounts in the presence of an oxidizing agent such as N-methylene-N-oxide, hydrogen peroxide or sodium tert-butylhydroperoxide, in a solvent such as tetrahydrofuran/water to give the corresponding glycol.

Reaction Scheme B:

As shown in Reaction Scheme B, a solution of the glycol is treated with an oxidizing agent such as lead tetracetate in a solvent such as toluene or benzene to give the corresponding aldehyde.

Reaction Scheme C:

As shown in Reaction Scheme C, the aldehyde may be obtained directly by treatment of the protected alkenyl-substituted macrolide with osmium tetroxide, in the presence of an oxidizing agent such as N-methylene-N-oxide followed by work up in the presence of sodium periodate.

Reaction Scheme D:

As shown in Reaction Scheme D, a solution of the aldehyde may be reacted with an unstabilized or stabilized Wittig reagent (wherein R is phenyl, $R^6$ and $R^7 = R^5$ absent the alpha-carbon atom, and $X^-$ is a negative counterion selected from chloro, bromo and iodo) to give the desired olefin derivative which is subsequently deprotected by treatment with hydrogen fluoride or HF-pyridine in acetonitrile or tetrahydrofuran.

Reaction Scheme E:

As shown in Reaction Scheme E, a solution of the protected aldehyde is treated with a carbon tetrahalide, such as carbon tetrabromide, carbon tetrachloride or carbon tetrafluoride (wherein X is halo) in the presence of triphenylphosphine to give the dihalo olefin which is subsequently deprotected as in Scheme D.

Reaction Scheme F:

As shown in Reaction Scheme F, a solution of the olefin derivative (wherein $R^{5a}$ contains an alkenyl group) is reduced to the corresponding alkane by reduction catalytically in the presence of hydrogen and a noble metal catalyst, such as rhodium on carbon, in a solvent such as methanol, ethanol, ethyl acetate, dichloromethane, dimethoxyethane or dimethylformamide.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereo isomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the Compounds Within the Scope of the Invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues such as heart, kidney, liver, duodenum, small-bowel, medulla ossium, skin, pancreatic islet-cell, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, allergic encephalomyelitis, glomerulonephritis, etc., and infectious diseases caused by pathogenic microorganisms.

The compounds of Formula I are also useful for treating inflammatory and hyperproliferative skin diseases and cutaneous manifestations of immunologically-mediated illnesses such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias or Alopecia areata. More particularly, the compounds of Formula I are useful in hair revitalizing, such as in the treatment of male pattern alopecia or alopecia senilis, by providing epilation prevention, hair germination, and/or a promotion of hair generation and hair growth.

The compounds of Formula I are further useful for treating reversible obstructive airways disease, including conditions such as asthma, including bronchial asthma, allergic asthma, intrinsic asthma, extrinsic asthma and dust asthma, particularly chronic or inveterate asthma (for example late asthma and airway hyper-responsiveness), bronchitis and the like. The compounds of Formula I may also be useful for treating hepatic injury associated with ischemia.

The compounds of Formula I are also useful for treating multidrug resistance of tumor cells, (i.e. enhancing the activity and/or sensitivity of chemotherapeutic agents), preventing or treating inflammation of mucosa or blood vessels, $LTB_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis, or intestinal lesions associated with thermal burns, cytomegalovirus infection, particularly HCMV infection, idiopathic thrombocytopenic purpura and Basedow's disease.

Further, the compounds of Formula I are also useful for treating or preventing renal diseases selected from interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases selected from hyperthyroidism; hematic diseases selected from pure red cell aplasia, aplastic anemia, hypoplastic anemia, autoimmune hemolytic anemia, agranulocytosis and anerythroplasia; bone diseases such as osteoporosis; respiratory diseases selected from sarcoidosis, fibroid lung and idiopathic interstitial pneumonia; eye diseases selected from herpetic keratitis, conical cornea, dystrophia epithelialis corneae, corneal leukmas, ocular pemphigus, Mooren's ulcer, scleritis and Grave's ophthalmopathy; skin diseases selected from dermatomyositis, leukoderma vulgaris, ichthyosis vulgaris, photoallergic sensitivity and cutaneous T cell lymphoma; circulatory diseases selected from arteriosclerosis, aortitis syndrome, polyarteritis nodosa and myocardosis; collagen diseases selected from scleroderma, Wegener's granuloma and Sjogren's syndrome; adiposis; eosinophilic fasciitis; periodontal disease; and muscular dystrophy.

The compounds of Formula I may also act as antagonists of macrocyclic immunosuppressive compounds, including derivatives of 12-(2'-cyclohexyl-1'-methylvinyl)-13,19,21,27-tetramethyl-11,28-dioxa-4-azatricyclo[22.3.1.0$^{4,9}$]octacos-18-ene, and so be useful in the treatment of immunodepression (such as AIDS, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428,169. Oral dosage forms may be prepared essentially as described by T. Hondo, et al., *Transplantation Proceedings*, 1987, XIX, Supp. 6, 17-22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For modifying the activity and/or toxicity of FK-506-type immunosuppressants, a compound of Formula I may be administered prior to, in conjunction with or subsequent to the administration of an FK-506-type of a compound.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably from 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

PREPARATION OF STARTING INTERMEDIATES

17-Allyl-1-hydroxy-12-[2'-(4''-t-butyldimethylsilyloxy-3''-methoxycyclohexyl)-1'-methylvinyl]-14-t-butyl-dimethylsilyloxy-23,25-dimethoxy-13,19,21,27-tetramethyl-11,28-dioxa-4-azatri-cyclo-[22.3.1.0$^{4,9}$]octacos-18-ene-2,3,10,16-tetraone To a cooled solution (0° C.) of 17-allyl-1,14-dihydroxy-12-[2'-(4''-hydroxy-3''-methoxycyclohexyl)-1'-methylvinyl]-23,25-dimethoxy-13,19,21,27-tetra-methyl-11,28-dioxa-4-azatricyclo[22.3.1.0$^{4,9}$]-octacos-18-ene-2,3,10,16-tetraone (395 mg) in dry methylene chloride (15 ml) was added 2,6-lutidine (160 mg) followed by t-butyldimethylsilyl triflouromethanesulfonate (250 mg). Reaction temperature was raised to r.t. and stirred under nitrogen atmosphere. After 6 hr, the reaction was quenched with 10 ml of water and extracted with ethyl acetate. Organic layer was washed (water, saturated NaHCO$_3$, saturated NaCl) and dried (anhydrous MgSO$_4$). Removal of solvent under reduced pressure gave the crude product.

EXAMPLE 1

17-[(1'''-Carboethoxy)prop-1'''-en3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of the protected aldehyde 17-ethanalyl-1-hydroxy-14-tertbutyldimethylsilyloxy-12-[2'-(4''-tert-butyl-dimethylsilyloxy-3''-methoxycyclohexyl)-1'-methyl-vinyl]-23,25-dimethoxy-13,19,21,27-tetramethyl-11,28-dioxa-4-aza-tricyclo-[22.3.1.0$^{4,9}$]octacos-18-ene-2,3,10,16-tetraone (54 mg) (prepared essentially as described in PCT Patent Publication No. WO 89/05304, Examples 19 and 20 and prior or subsequent protection by treatment with t-butyldimethylsilyl triflu-oromethanesulfonate) in dichloromethane (1 ml) at ambient temperature was added (carboethoxymethylene) triphenylphosphorane (20 mg) and the solution stirred for three hours. The reaction mixture was then filtered through a pad of silica gel and purified by column chromatography on silica gel eluting with 80% hexane: 20% acetone to give 17-[(1'''-carboethoxy)prop-1'''-en-3'''-yl ]-1-hydroxy-14-tertbutyldimethylsilyloxy-12-[2'-(4''-tert-butyldimethylsilyloxy-3''-methoxycyclohexyl)-1'-methylvinyl]-23,25-dimethoxy-13,19,21,27-tetramethyl-11,28-dioxa-4-aza-tricylclo[22.3.1.0$^{4,9}$]octacos-18-ene-2,3,10,16-tetraone (46 mg). This was then dissolved in acetonitrile (2.65 ml) and treated with 48% aqueous hydrogen fluoride (0.23 ml) at ambient temperature for two hours. The reaction was quenched by the addition of saturated aqueous sodium bicarbonate solution and when effervescence had ceased the reaction mixture was extracted with ethyl acetate. Purified by column chromatography on silica gel eluting with 50% hexane: 50% acetone to give the title compound (26 mg).

MS(FAB) 898 (M$^+$ +Na)

partial $^1$H NMR δ: 6.80 (m, 1H); 5.79 (dm, J=15 Hz, 1H).

EXAMPLE 2

17-[(1'''-Carbomethoxy)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone Prepared essentially by the procedure of Example 1 using (carbomethoxymethylene) triphenylphosphorane as the alkylating agent to give the title compound (13 mg) as a white solid.

MS(FAB) 868 (M+ +Li)

EXAMPLE 3

17-[(2'''-Carboethoxy)but-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone Prepared essentially by the procedure of Example 1 using (carboethoxyethylidene) triphenylphosphorane as the alkylating agent to give the title compound (28 mg) as a white solid.

MS(FAB) 912 (M+ +Na)

partial $^1$NMR δ: 6.61 (m, 1H); 5.29 (s, 1H major); 5.13 (s, 1H minor); 5.02 (m, 2H).

EXAMPLE 4

17-[1'''-Oxobut-2'''-en-4'''-yl]-1,14-dihydroxy--12-[2'-(4''-hydroxy-3''-methoxycyclohexyl)-1'-methylvinyl]-23,25-dimethoxy-13,19,21,27-tetramethyl-11,28-dioxa-4-aza-tricylclo[22.3.1.0$^{4,9}$]octacos-18-ene-2,3,10,16-tetraone To a solution of the aldehyde 17-ethanalyl-1-hydroxy-14-tertbutyldimethylsilyloxy-12-[2'-(4''-tert-butyl-dimethylsilyloxy-3''-methoxy-cyclohexyl)-1'-methyl-vinyl]-23,25-dimethoxy-13,19,21,27-tetramethyl-11,28-dioxa-4-aza-tricylclo-[22.3.1.0$^{4,9}$]octacos-18-ene-2,3,10,16-tetraone (81 mg) in acetonitrile (2.1 ml) at 60° C. was added (triphenylphosphoranylidene) acetaldehyde (5 eq., 119 mg) in small portions over the space of 6 hrs. The reaction mixture was filtered through a silica gel pad washing with ethyl acetate, and concentrated. Purified by column chromatography on silica gel eluting with 80% hexane:20% acetone to give 17-[1'''-oxobut-2'''-en-4'''-yl]-1-hydroxy-14-tert-butyldimethylsilyloxy-12-[2'-(4''-tert-butyldimethylsilyloxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (66 mg). This aldehyde (58 mg) was then dissolved in acetonitrile (1 ml) at 0° C. and treated with 48% hydrogen fluoride (4 drops) and stirred to room temperature for 1 hour. The reaction was then quenched with saturated sodium bicarbonate solution and extracted with ethyl acetate. The combined organic extracts were dried (MgSO$_4$), concentrated and purified by column chromatography on silica gel eluting with 60% hexane: 40% ethyl acetate to give the title compound as a white solid (23 mg).

MS(FAB) 854 (M+ +Na)

partial $^1$H NMR δ: 9.42 (d, J=6.6 Hz, 1H major); 9.42 (d, J=6.6 Hz, 1H minor); 6.70 (dt, J=15 Hz, 7.2 Hz, 1H); 6.08 (dt, J=15, 6.6 Hz, 1H).

EXAMPLE 5

17-[2'''-Oxopent-3'''-en-5'''-yl]-1,14-dihydroxy--12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,20,16-tetraone Prepared essentially by the procedure of Example 4 using 1-triphenylphosphoranylidene-2-propanone as the alkylating agent to give the title compound (11 mg) as a white solid.

MS(FAB) 852 (M+ +Li)

partial $^1$H NMR δ: 6.65 (m, J=7.2 Hz, 1H); 6.05 (d, J=17 Hz, 1H).

EXAMPLE 6

17-[2'''-Oxopent-5'''-yl]-1,-14-dihydroxy-12-[2'-(4''-hydroxy-3''-methoxycyclohexyl)-1'-methylvinyl]-23,25-di-methoxy-13,19,21,27-tetramethyl-11,28-dioxa-4-aza-tricylclo[22.3.1.0$^{4,9}$]octacos-18-ene-2,3,10,16-tetraone To a solution of 17-[2'''-oxopent-3'''-en-5'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (34 mg) in dry toluene (1.5 ml) was added acetic acid (3 ml) and tetrakis triphenylphosphinepalladium (3 mg) and the reaction stirred for 5 minutes before the addition of tri-n-butyltin hydride (12 ml). The reaction was then stirred at r.t. in the dark for 2 hours before being quenched by the addition of brine and extracted with ether. The ether extracts were dried (MgSO$_4$) and filtered through a silica gel pad before concentrating. The crude material was then dissolved in acetonitrile and washed with hexane to remove tin residues. The acetonitrile layer was concentrated and purified by column chromatography on silica gel eluting with 80% hexane: 20% acetone to give 7-[2'''-oxopent-5'''-yl]-1-hydroxy-14-tert-butyldimethylsilyloxy-12-[2'-(4''-tert-butyldimethylsilyloxy-3''-methoxycyclohexyl)-1'-methylvinyl]-23,25-dimethoxy-13,19,21,27-tetramethyl-11,28-dioxa-4-azatricylclo [22.3.1.0$^{4,9}$]octacos-18-ene-2,3,10,16-tetraone (22 mg). This was dissolved in acetonitrile (1 ml) at 0° C. and treated with 48% aqueous hydrogen fluoride (1 drop) and stirred for 2 hours before being quenched by the addition of saturated sodium bicarbonate solution. Extraction with ethyl acetate and further purification by column chromatography on silica gel eluting with 50% hexane:50% acetone yielded the title compound as a white solid (11 mg).

MS(FAB) 870 (M+ +Na)

partial $^1$H NMR δ: 5.30 (s, 1H major); 5.18 (s, 1H minor); 5.00 (m, 2H); 4.78 (s, 1H minor); 4.60 (d, J=4.5 Hz, 1H); 4.40 (d, J=15 Hz, 1H); 4.30 (s, 1H major).

EXAMPLE 7

17-[1'''-Hydroxybut-2'''-en-4'''-yl]-1,14-dihydroxy--12-[2'-(4''-hydroxy-3''-methoxycyclohexyl)-1'-methylvinyl]-23,25-dimethoxy-13,19,21,27-tetramethyl-11,28-dioxa-4-aza-tricylclo[22.3.1.0$^{4,9}$]octacos-18-ene-2,3,10,16-tetraone To a solution of 17-[1'''-oxobut-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos- 18-ene-2,3,10,16-tetraone (20 mg) in THF (2 ml) at −78° C. under nitrogen was added lithium tris[(3-ethyl-3-pentyl)-oxy]-aluminum hydride (0.15 ml) dropwise, slowly. When the addition was complete the reaction was quenched by adding saturated ammonium chloride solution, extracted with ethyl acetate and dried (MgSO4). Purified by column chromatography on silica gel eluting with 80% hexane: 20% acetone to give 7 -[1''''-hydroxybut-2'''-ene-4'''-yl]-1-hydroxy-14-tert-butyldimethylsilyl-oxy-12-[2'-(4''-tert-butyldimethylsilyloxy-3''-methoxy-cyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (4.6 mg). This was then deprotected in the usual manner with 48% aqueous hydrogen fluoride to give the title compound as a white solid (1 mg).

MS(FAB) 856 (M+ +Na)

partial $^1$H NMR δ: 5.62 (m, 2H); 5.30 (s, 1H major); 5.17 (s, 1H minor); 5.02 (m, 2H).

EXAMPLE 8

17-(1''',1'''-Dibromo)allyl-1,14-dihydroxy-12-[2'-(4''-hydroxy-3''-methoxycyclohexyl)-1'-methylvinyl]-23,25-di-methoxy-13,19, 21,27-tetramethyl-11,28-dioxa-4-aza-tricylclo[22.3.1.0$^{4,9}$]octacos-18-ene-2,3,10,16-tetraone To a solution of the aldehyde 17-ethanalyl-1-hydroxy-14-tertbutyldimethylsilyloxy-12-[2'-(4''-tert-butyl-dimethylsilyloxy-3''-methoxy-cyclohexyl)-1'-methyl-vinyl]-23,25-dimethoxy-13,19,21,27-tetramethyl-11,28-dioxa-4-aza-tricylclo-[22.3.1.0$^{4,9}$]octacos-18-ene-2,3,10,16-tetraone (50 mg) and triphenylphosphine (56 mg) in dichloromethane (0.5 ml) at 0° C. was added carbon tetrabromide in dichloromethane (0.5 ml) dropwise. When the addition was finished the reaction was quenched by the addition of hexane and filtration through a silica gel pad washing with hexane and ether. The washes were concentrated and purified by column chromatography on silica gel eluting with 90% hexane: 10% acetone to give 7-(1''',1'''-bromo)allyl-1-hydroxy-14-tert-butyldimethylsilyloxy-12-[2'-(4''-tert-butyldimethylsilyloxy-3''-methoxycyclohexyl)-1'-methyl-vinyl]-23,25-dimethoxy-13,19,21,27-tetramethyl-11,28-dioxa-4-azatricylclo[22.3.1.0$^{4,9}$]octacos-18-ene-2,3,10,16-tetraone (40 mg). This was then deprotected in the usual manner with 48% aqueous hydrogen fluoride to give the title compound as a white solid (24 mg).

MS(FAB) 968 (M+ +Li)

partial $^1$H NMR δ: 6.32 (m, 1H); 5.30 (s, 1H major); 5.16 (s, 1H minor).

EXAMPLE 9

17-(1''',1''''-Dichloro)allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-aza-tricylclo[22.3.1.0$^{4,9}$]octacos-18-ene-2,3,10,16-tetraone Prepared essentially by the procedure of Example 8 using bromotrichloromethane as the alkylating agent to give the title compound as a white solid (10 mg).

MS(FAB) 878 (M+ +Li)

partial $^1$H NMR δ: 5.75 (m, 1H); 5.40 (s, 1H major); 5.16 (s, 1H minor); 5.03 (m, 2H); 4.72 (s, 1H minor); 4.65 (d, J=4.7 Hz, 1H).

EXAMPLE 10

17-[(1''''-Phenyl)prop-1'''-en-3'''-yl]-1,14-dihydroxy--12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone To a solution of benzyltriphenylphosphonium chloride (147 mg) in toluene (1 ml) at ambient temperature under nitrogen atmosphere was added 0.5M potassium bis(trimethylsilyl)amide in toluene (610 ul). The solution was stirred at ambient temperature for 10 minutes then cooled to −78° C. A solution of the aldehyde (79 mg) in toluene (1.5 ml) was added dropwise and the resulting solution stirred for 15 minutes. The reaction mixture was quenched with aqueous ammonium chloride and extracted with ether. The organic extracts were dried and concentrated. The residue was purified by flash chromatography on silica gel (90:10 hexane-acetone) to yield 17-[(1'''-phenyl) prop-1'''-ene-3'''-yl]-1-hydroxy-14-tert-butyldimethylsilyloxy-12-[2'-(4''-tert-butydimethylsilyloxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone (37 mg). This was then dissolved in tetrahydrofuran (0.5 ml) and treated with hydrogen flouride-pyridine (15 drops) at ambient temperature for six hours; more hydrogen fluoride-pyridine (15 drops) was added and the solution stirred for twenty hours more. The reaction was quenched by diluting with diethyl ether and washing with water, then with aqueous sodium bicarbonate solution. The aqueous washes were combined and extracted with ether, the combined organics were dried and concentrated. The residue was purified on silica gel (70:30 hexane-acetone) to yield the title compound (26 mg).

MS(FAB) 886 (M+Li)

partial $^1$H NMR δ: 7.15 (m, 5H); 6.44 (minor component, d, J=12.5 Hz); 6.37 (major component, 1H, d, J=17.5 Hz); 6.18 (m, 1H)

EXAMPLE 11

17-[Pent-1''',3'''-dien-5'''-yl]-1,14-dihydroxy-12-[2'-(4''-hydroxy-3''-methoxycyclohexyl)-1'-methylvinyl]-23,25-di-methoxy-13,19,21,27-tetramethyl-11,28-dioxa-4-azatricylclo[22.3.1.0$^{4,9}$]octacos-18-ene-2,3,10,16-tetraone Prepared essentially by the procedure of Example 10 using allyltriphenylphosphonium bromide as the Wittig salt to yield the title compound (9 mg).

MS(FAB) 836 (M+Li)

partial $^1$H NMR δ: 6.68 (m, 1H); 6.22 (m, 1H); 6.02 (m, 2H)

EXAMPLE 12

17-[But-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0$^{4,9}$]octacos-18-ene-2,3,10,16-tetraone Prepared essentially by the procedure of Example 10 using ethyltriphenylphosphonium bromide as the Wittig salt to yield the title compound (23 mg).

MS(FAB) 824 (M+Li)

partial $^1$H NMR δ: 5.48 (m, 1H); 5.29 (m, 1H)

EXAMPLE 13

17-[Hex-4'''-en-6'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially by the procedure of Example 10 using butyltriphenylphosphonium bromide as the Wittig salt to yield the title compound (34 mg).
MS(FAB) 852 (M+Li)
partial $^1$H NMR δ: 5.39 (m, 1H); 5.26 (m, 1H)

EXAMPLE 14

17-[Oct-6'''-en-8'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially by the procedure of Example 10 using hexyltriphenylphosphonium bromide as the Wittig salt to yield the title compound (9 mg).
MS(FAB) 880 (M+Li)
partial $^1$H NMR δ: 4.9–5.5 (m, 5H)

EXAMPLE 15

17-[Pent-3'''-en-5'''-yl]--1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially by the procedure of Example 10 using propyltriphenylphosphonium bromide as the Wittig salt to yield the title compound (23 mg).
MS(FAB) 838 (M+Li)
partial $^1$H NMR δ: 4.95–5.45 (m, 5H)

EXAMPLE 16

17-[(1''',1'''-Dimethyl)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially by the procedure of Example 10 using isopropyltriphenylphosphonium bromide as the Wittig salt to yield the title compound (10 mg).
partial $^1$H NMR δ: 5.07 (d, 1H, J=9.2 Hz); 4.95–5.05 (m, 2H)

EXAMPLE 17

17-[1-Butyl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-[But-2'''-en-4'''-yl]-1-,14-dihydroxy-12-[2'-(4''-hydroxy-3''-methoxycyclohexyl)-1'-methylvinyl]-23,25-di-methoxy-13,19,21,27-tetramethyl-11,28-dioxa-4-azatricyclo[22.3.1.0$^{4,9}$]octacos-18-ene-2,3,10,16-tetraone (35 mg) was dissolved in ethyl acetate (1 mL) and rhodium on carbon (9 mg) was added. The system was flushed out with hydrogen three times then maintained under hydrogen for thirty minutes. The reaction was worked up by filtration through celite and concentration to yield the title compound (32 mg).
MS(FAB) 826 (M+Li)
partial $^1$H NMR δ: 5.30 (s, 1H, major rotamer); 5.17 (s, 1H, minor rotamer); 4.95–5.1 (overlapping m, 2H)

EXAMPLE 18

17-[1-Pentyl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone 17-[Pent-3'''-en-5'''-yl]--1,14-dihydroxy-12-[2'-(4''-hydroxy-3''-methoxycyclohexyl)-1'-methylvinyl]-23,25-di-methoxy-13,19,21,27-tetramethyl-11,28-dioxa-4-azatricyclo[22.3.1.0$^{4,9}$]octacos-18-ene-2,3,10,16-tetraone (24 mg) was hydrogenated by essentially the procedure of Example 17 to yield the title compound (17 mg).
MS(FAB) 840 (M+Li)
partial $^1$H NMR δ: 5.30 (s, 1H, major rotamer); 5.17 (s, 1H, minor rotamer); 4.95–5.1 (overlapping m, 2H)

EXAMPLE 19

17-[But-1'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The aldehyde was reacted via the aforementioned Wittig procedure (Example 17) using methoxymethyltriphenylphosphonium chloride as the Wittig salt to yield 17-[(1'''-methoxy)prop-1'''-en-3'''-yl]-1-hydroxy-14-tert-butyl-dimethylsilyloxy-12-[2'-(4''-tert-butyldimethyl-silyl-oxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. This new product (85 mg) was treated with p-toluene- sulfonic acid (5 mg) in dichloromethane (1 mL) for 15 minutes followed by workup with aqueous sodium bicarbonate solution and extraction with ether. The combined organic extracts are dried, concentrated and purified by flash chromatography (silica gel, 90:10 hexane-acetone) to yield 17-[(1'''--methoxy)prop-1'''-ene-3'''-yl]-1-hydroxy-14-tert-butyldimethylsilyloxy-12-[2'-(4''-tert-butyldimethylsilyloxy-3''-methoxycyclohexyl)-1'-methylvinyl]-23,25-dimethoxy-13,19,21,27-tetra-methyl-11,28-dioxa-4-azatricyclo[22.3.1.0$^{4,9}$]octacos-18-ene-2,3,10,16-tetraone (27 mg).

This new aldehyde (27 mg) was reacted via the Wittig procedure using methyltriphenylphosphonium bromide as the salt to yield 17-[but-1'''-en-4'''-yl]-1-hydroxy-14-tert-butyldimethylsilyloxy-12-[2'-(4''-tert-butyl-dimethylsilyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (12 mg). This compound (16 mg) was treated with hydrogen fluoride-pyridine (0.2 mL) in tetrahydrofuran (0.5 mL) at ambient temperature for 19 hours. Workup was done by diluting with ether then washing with water followed by aqueous sodium bicarbonate solution. The aqueous washes were combined and extracted with ether. The combined organic phases were dried and concentrated, the residue then purified on silica gel (60:40 hexane-acetone) to yield the title compound (3 mg).
MS(FAB) 824 (M+Li)
partial $^1$H NMR δ: 5.73 (m, 1H); 5.30 (major rotamer, s, 1H); 5.17 (minor rotamer, s, 1H); 4.9–5.1 (m, 3H)

EXAMPLE 20

17-[1'''-Carboxymethyl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethanalyl-1-hydroxy-14-tert--butyldimethylsilyloxy-12-[2'-(4''-tert-butyldimethylsiliyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg) and 2-methyl-2-butene (0.242 ml) in tert-butanol (1 ml) and tetrahydrofuran (4 drops) at ambient temperature was added sodium chlorite (41 mg) and sodium dihydrogen phosphate (41 mg) in water (0.5 ml) over 10 minutes. The reaction was complete upon addition of the sodium chlorite mixture and was quenched by the addition of saturated ammonium chloride solution and extracted into ethyl acetate. The crude material was purified by column chromatography on silica gel eluting with 70% hexane: 30% acetone to give 17-ethanalyl-1-hydroxy-14-tert-butyldimethylsilyloxy-12-[2'-(4''-tert-butyldimethylsiliyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (24 mg). This was dissolved in tetrahydrofuran (300 μl) and treated with hydrogen fluoride/pyridine (8 drops) and stirred for 24 hours. The reaction was quenched by the addition of saturated sodium bicarbonate solution and then re-acidified to pH5–6 with 2M hydrochloric acid. The product was extracted with ethyl acetate, dried (MgSO$_4$) and concentrated before being purified by column chromatography on silica gel eluting with 90% dichloromethane: 10% methanol containing a trace of acetic acid to give the title compound as a white solid (14 mg).

EXAMPLE 21

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5 \times 10^5$ cells/ml in complete culture medium composed of RPMI 1640 medium with 10% heat-inactivated fetal calf serum, 100 mM glutamine, 1 mM sodium pyruvate, $2 \times 10^{-5}$M 2-mercaptoethanol and 50 μg/ml gentamycin. Ionomycin was added at 250 ng/ml and PMA at 10 ng/ml. The cell suspension was immediately distributed into 96 well flat-bottom microculture plates (Costar) at 200 μl/well. The various dilutions of the compound to be tested were then added in triplicate wells at 20 μl/well. The compound 17-allyl-1,14-dihydroxy-12-[2'-(4''-hydroxy-3''-methoxy cyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 μCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Betacounter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay: 8, 9, 12, 17, 18 and 19.

For determining antagonist activity, the foregoing procedure is modified in that dilutions of compounds are cultured with 17-ally-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (as a standard) at a concentration of 1.2 nM, a concentration which inhibits T cell proliferation by 100%, the concentration of compound required to reverse the inhibition obtained by the standard alone by 50% is measured, and the ED$_{50}$ value is determined.

A selection of compounds were tested according to the previous procedure. The title compounds of the following Examples had activity in reversing the inhibition of T-cells by the standard: 1, 2, 3, 4, 5, 6, and 7.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula I:

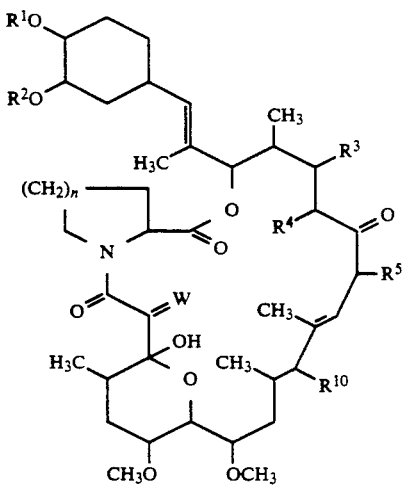

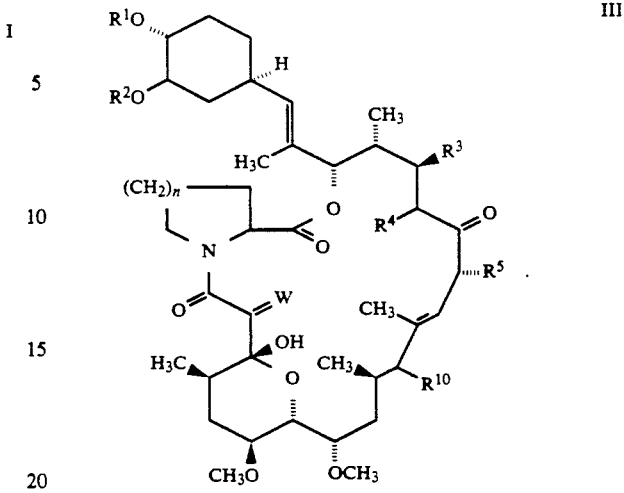

or a pharmaceutically acceptable salt thereof, wherein:

$R^1$ is selected from:
  (1) hydrogen; and
  (2) $C_{1-4}$ alkanoyl;

$R^2$ is selected from:
  (1) methyl; and
  (2) hydrogen;

$R^3$ is hydrogen, hydroxy, or $C_{1-6}$ alkoxy;

$R^4$ is hydrogen, or $R^3$ and $R^4$ taken together form a double bond;

$R^5$ is selected from:
  (1) $C_{4-8}$ alkyl substituted with one or more substituents selected from:
    (a) phenyl,
    (b) hydroxy,
    (c) halo,
    (d) —CHO,
    (e) —CO$_2$H,
    (f) —CO$_2$—C$_{1-6}$alkyl;
  (2) $C_{3-8}$ alkenyl substituted with one or more substituents selected from:
    (a) phenyl,
    (b) hydroxy,
    (c) halo,
    (d) —CHO,
    (e) —CO$_2$H,
    (f) —CO$_2$—C$_{1-6}$alkyl;

$R^{10}$ is hydrogen, hydroxy, or fluoro;

W is O or (H, OH);

n is 1 or 2.

2. The compound according to claim 1 wherein the absolute configuration of Formula I is as defined in Formula III:

3. A compound which is selected from the group consisting of:

17-[(1'''-carboethoxy)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#1)

17-[(1'''-carbomethoxy)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#2)

17-[(2'''-carboethoxy)but-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#3)

17-[1'''-oxobut-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#4)

17-[2'''-oxopent-3'''-en-5'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#5)

17-[2'''-oxopent-5'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#6)

17-[1'''-hydroxybut-2'''-en-4'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#7)

17-(1''',1'''-dibromo)allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyIclo[22.3.1.0$^{4,9}$]octacos-18-ene-2,3,10,16-tetraone; (#8)

17-(1''',1'''-dichloro)allyl-1,14-dihydroxy-12-[2'-(4''-hydroxy-3''-methoxycyclohexyl)-1'-methylvinyl]-23,25-dimethoxy-13,19,21,27-tetramethyl-11,28- dioxa-4-azatricylclo[22.3.1.0⁴,⁹]octacos-18-ene-2,3,10,16-tetraone; (#9)

17-[(1'''-phenyl)prop-1'''-en-3'''-yl]-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricylclo[22.3.1.0⁴,⁹]octacos-18-ene-2,3,10,16-tetraone (#10).

4. A compound which is:

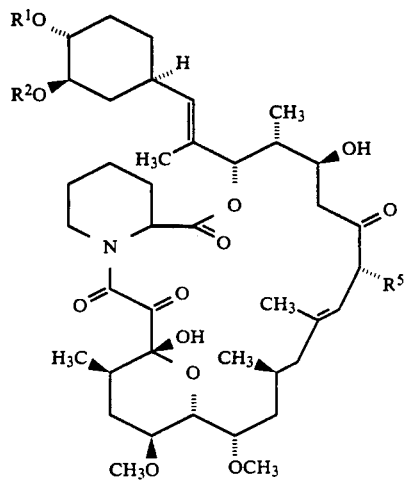

wherein $R^1$, $R^2$ and $R^5$ are selected from the following combinations of substituents:

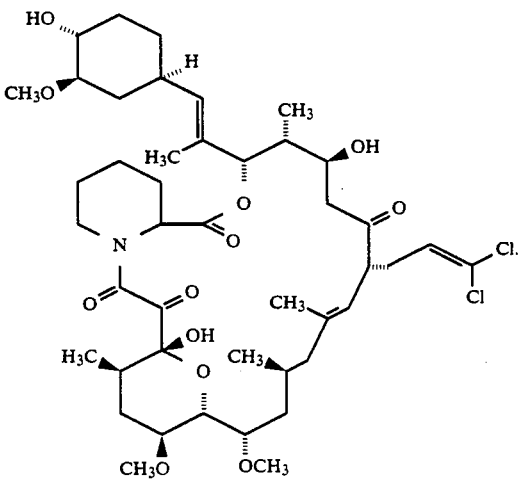

|     | $R^1$ | $R^2$ | $R^5$ |
|-----|-------|-------|-------|
| (a) | H | CH₃ | ⤳CO₂Et (with methyl) |
| (b) | H | CH₃ | ⤳CO₂Et |
| (c) | H | CH₃ | ⤳CO₂Me |
| (d) | H | CH₃ | ⤳CHO |
| (e) | H | CH₃ | ⤳C(=O)CH₃ |
| (f) | H | CH₃ | ⤳CH₂C(=O)CH₃ |
| (g) | H | CH₃ | ⤳CH₂OH |
| (h) | H | CH₃ | ⤳CCl=CCl |
| (i) | H | CH₃ | ⤳CBr=CHBr |
| (j) | H | CH₃ | ⤳CH=CH-Ph |

5. The compound of claim 4 which is:

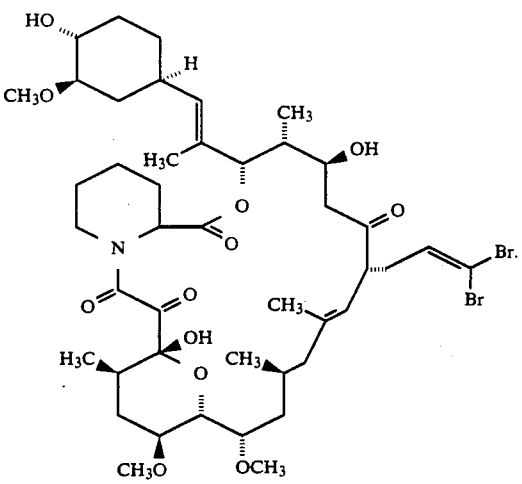

6. The compound of claim 4 which is:

7. A pharmaceutical composition comprising a pharmaceutical carrier and a therapeutically effective amount of the compound of claim 1.

8. A method for the treatment of immunoregulatory disorders or diseases comprising the administration to a mammalian species in need of such treatment of an effective amount of the compound of claim 1.

* * * * *